United States Patent
Sattur et al.

(10) Patent No.: US 6,822,003 B2
(45) Date of Patent: Nov. 23, 2004

(54) ALDOSE REDUCTASE INHIBITOR AND PROCESS FOR PREPARATION THEREOF

(75) Inventors: Avinash Prahalad Sattur, Karnataka (IN); Kadiyala Chandrasekhar Rao, Karnataka (IN); Kilaru Naveen Babu, Karnataka (IN); Divakar Soundar, Karnataka (IN); Naikanakatte Ganesh Karanth, Karnataka (IN); Ramachandraiah Shamala Tumkur, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 181 days.

(21) Appl. No.: 10/024,574

(22) Filed: Dec. 21, 2001

(65) Prior Publication Data

US 2003/0134399 A1 Jul. 17, 2003

(51) Int. Cl.[7] .......................... A61K 31/122; C12P 1/00; C12P 21/04; C12N 9/02
(52) U.S. Cl. .................. 514/682; 435/41; 435/69.2; 435/189
(58) Field of Search .................. 435/41, 69.2, 189; 514/682

(56) References Cited

PUBLICATIONS

Boghosian, Robert A. and McGuinness, Eugene T. Pig Brain aldose reductase: A kinetic study—. 1981. International J. Biochemistry, 13(8), pp. 909–914.*

Wittenveen, C.F.B. et al. L–arabinose and D–xylose catabolism in Aspergillus niger, 1989. J. General Microbiology, 135(8), pp. 2163 to 2171.*

* cited by examiner

*Primary Examiner*—Jon P. Weber
*Assistant Examiner*—Kailash C. Srivastava
(74) *Attorney, Agent, or Firm*—Nixon & Vanderhye P.C.

(57) ABSTRACT

Aldose redcutase inhibitor and pharmaceutically acceptable derivatives thereof of the formula I below derived from cultures of *Aspergillus niger* CFR 1046 and useful as a rat lens aldose reductase inhibitor

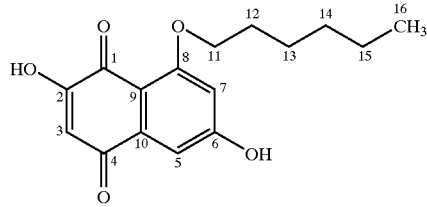

14 Claims, 3 Drawing Sheets

ALDOSE REDUCTASE INHIBITOR AND PROCESS FOR PREPARATION THEREOF

FIELD OF THE INVENTION

The present invention relates to a novel aldose reductase inhibitor. More particularly, the present invention relates to a novel aldose reductase inhibitor of formula I derived from cultures of *Aspergillus niger* CFR 1046 and pharmaceutically acceptable derivatives thereof.

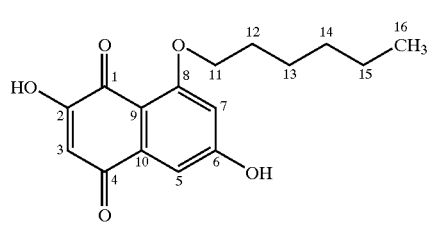

BACKGROUND OF THE INVENTION

Diabetes mellitus and its disabling complications which include blindness, renal failure, limb amputation, myocardial infarction affect millions of people (Schumacher, M. P. *Diabetes* 44 (1995)1355–1361). In the absence of or in cases of insufficient insulin, glucose accumulates in the blood of diabetics. Certain cells such as those in the peripheral nerves, the lens of the eye, or parts of the kidneys, however, do not need insulin to get glucose. As a result, maximum damage such as blindness, neuropathy and kidney damage occurs in such sites in diabetics. Nerve damage in diabetes is largely caused by loss of the insulating myelin sheath around nerves, which in turn causes message transmission to be erratic and painful, or non-existent. The reason this occurs is that when glucose enters these cells, it is converted into sorbitol by the enzyme aldose reductase (Alditol: $NADP^+$ 1-oxidoredutase, EC 1.1.1.21) which catalyses the NADPH-linked reduction of a broad group of aldoses to respective alduronic acids (Wilson K. W., Boren K. M. and Gabbay K. H., *Science* 257 (1992) 3). Sorbitol is then slowly converted into fructose by sorbitol dehydrogenase. Neither sorbitol nor fructose can cross the membrothe and leave the cell easily, thereby causing damage as they accumulate. The resulting changes include changes in osmotic pressures, alterations in redox state of pyridine nucleotides (increased $NADH/NAD^+$ ratio) and depleted intracellular levels of myoinositol (Larson E R, Lipinski C A and Sarges R *Med Res Revs* 8 (1988) 159–186).

Since diabetics have larger than normal amounts of glucose in the blood, the damage can lead to the above-mentioned problems. Certain substances present naturally in foods, block aldose reductase and prevent cell damage. Vitamin C, Alpha Lipoic Acid, Licorice, and various citrus or other antioxidants, e.g. quercetin, are aldose reductase inhibitors (Kim H. Y. and Oh J. H., *Biosci. Biotech. Biochem* 63 (1999) 184–188). Inhibitors against these enzymes thus have a potential application in both the food and medical sector.

Traditionally in Japan, some kampo medicines (traditional oriental herbal prescriptions) have long been used for the treatment of diabetic neuropathy (Aida, K, Tawata, M., Shindo, H., Onaya, T., Sasaki H., Yamaguchi, T., Chin, M., Mitsuhashi. *Planta Med*, 56 (1990) 254–258). The authors investigated the components of *Glycyrrhizae radix*, a constituent of some kampo medicines, and isolated six compounds (GUs 9–17). Among these, GU-17, identified as isoliquiritigenin, had the most potent aldose reductase inhibiting activity.

Isoliquiritigenin inhibited rat lens aldose reductase with an $IC_{50}$ of $3.2 \times 10(-7)$ M, using DL-glyceraldehyde as a substrate. It inhibited sorbitol accumulation in human red blood cells in vitro, with an $IC_{50}$ of $2.0 \times 10(-6)$ M. Isoliquiritigenin, when administered via an intragastric tube to diabetic rats, suppressed sorbitol accumulation in the red blood cells, the sciatic nerve, and the lens as effectively as ONO-2235. These results suggest that isoliquiritigenin may be effective in preventing diabetic complications.

Among the natural compounds, flavonoid compounds such as quercetin, quercetrin, naringinin and hesperidin are reported to be useful and potent aldose reductase inhibitors (Aida, K., Tawata, M., Shindo, H., Onaya, T., Sasaki H., Yamaguchi T., Chin, M., Mitsuhashi. *Planta Med*, 56 (1990) 254–258).

The presently known chemically synthesized aldose reductase inhibitors are Tolrestat, a chemically synthesised inhibitor with an $IC_{50}$ of $3.5 \times 10^{-8}$ M; and Sorbinil (Hollis H D, Johnson J L and Werbel L M. *J Med Chem*. 27 (1984) 255–256).

Some inhibitors obtained through the fermentation route are Thiazocins obtained from the fermented broth of Actinosynnema sp (Ozasa T, Yoneda T, Hirasawa M, Suzuki K, Tanaka K, Kadota S and Iwanami M. *J Antibiot* 44 (1991) 768–773), Thermorubrin and 2-hydroxy acetic acid from Thermoactinomyces sp UTA 8 (Hayashi K, Dombou M, Sekiya M, Nakajima H *J. of Antibiot*. 48 (1995) 1345–1346), Salfredins from Crucibulum sps (Matsumoto K, Nagashima K, Kamigauchi T, *J of Antibiot*. 48 (1995) 439–446) and YUA001 from Corynebacterium sp (Bahn Y, Park J, Bai D, Takase S, Yu J, *J of Antibiot*. 51 (1998) 902–907) which has an $IC_{50}$ of 1.8 mM against pig kidney aldose reductase.

The search is constantly on for new sources of aldose reductase inhibitors from natural sources that are inexpensive and show better activity.

OBJECTS OF THE INVENTION

It is an object of the invention to locate and identify new natural sources for aldose reductase inhibitors that are more economical and show better activity.

It is another object of the invention to provide new aldose reductase inhibitors that show improved activity and are obtained from natural sources.

A further object of the invention is to provide process for the extraction of aldose reductase inhibitors that are economical and more efficient.

SUMMARY OF THE INVENTION

These and other objects of the invention are achieved by a novel aldose reductase inhibitor derived through the fermentation of certain microorganisms.

Accordingly, the present invention relates to a novel aldose reductase inhibitor of the formula I below and its pharmaceutically acceptable derivatives

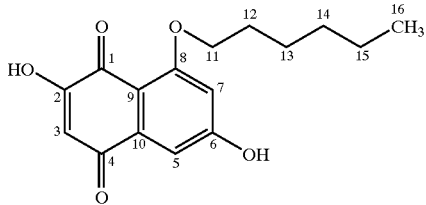

In one embodiment of the invention, the aldose reductase inhibitor is a rat lens aldose reductase inhibitor.

In another embodiment of the invention, the aldose reductase inhibitor of formula I is 2, 6, dihydroxy, 8, hexoxy, 1, 4, naphthaquinone.

The invention also relates to a process for the isolation of a novel aldose reductase inhibitor of the formula I below

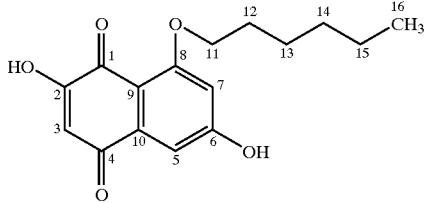

the process comprising culturing *Aspergillus niger* CFR 1046 and isolating said aldose reductase inhibitor.

In another embodiment of the invention, the aldose reductase inhibitor isolated from *Aspergillus niger* CFR 1046 is 2, 6, dihydroxy, 8, hexoxy, 1, 4, naphthaquinone.

In one embodiment of the invention, the aldose reductase inhibitory compound of formula I is isolated from *Aspergillus niger* CFR 1046 by fermentation.

In another embodiment of the invention, naphthaquinone is isolated from fermentates of *Aspergillus niger* CFR 1046 by solvent extraction.

In another embodiment of the invention, naphthaquinone is isolated from fermentates of *Aspergillus niger* CFR 1046 by column chromatography.

In another embodiment of the invention, naphthaquinone is isolated from fermentates of *Aspergillus niger* CFR 1046 by crystallization.

In a further embodiment of the invention, the compound of formula I is extracted from *Aspergillus niger* CFR 1046 from fermented potato dextrose broth using ethyl acetate solvent followed by column chromatography and crystallization.

In another embodiment of the invention, the compound of formula I isolated from *Aspergillus niger* CFR 1046 is converted to a pharmaceutically acceptable derivative.

In a further embodiment of the invention, the pharmaceutically acceptable derivative comprises acid or base addition products such as salts of this compound are also useful.

In a further embodiment of the invention, the addition products contain hydrochloride, hydrobromide, sulfate, sodium, potassium, calcium and the like ions.

BRIEF DESCRIPTION OF THE ACCOMPANYING DRAWINGS

DETAILED DESCRIPTION OF THE INVENTION

Figure 1:
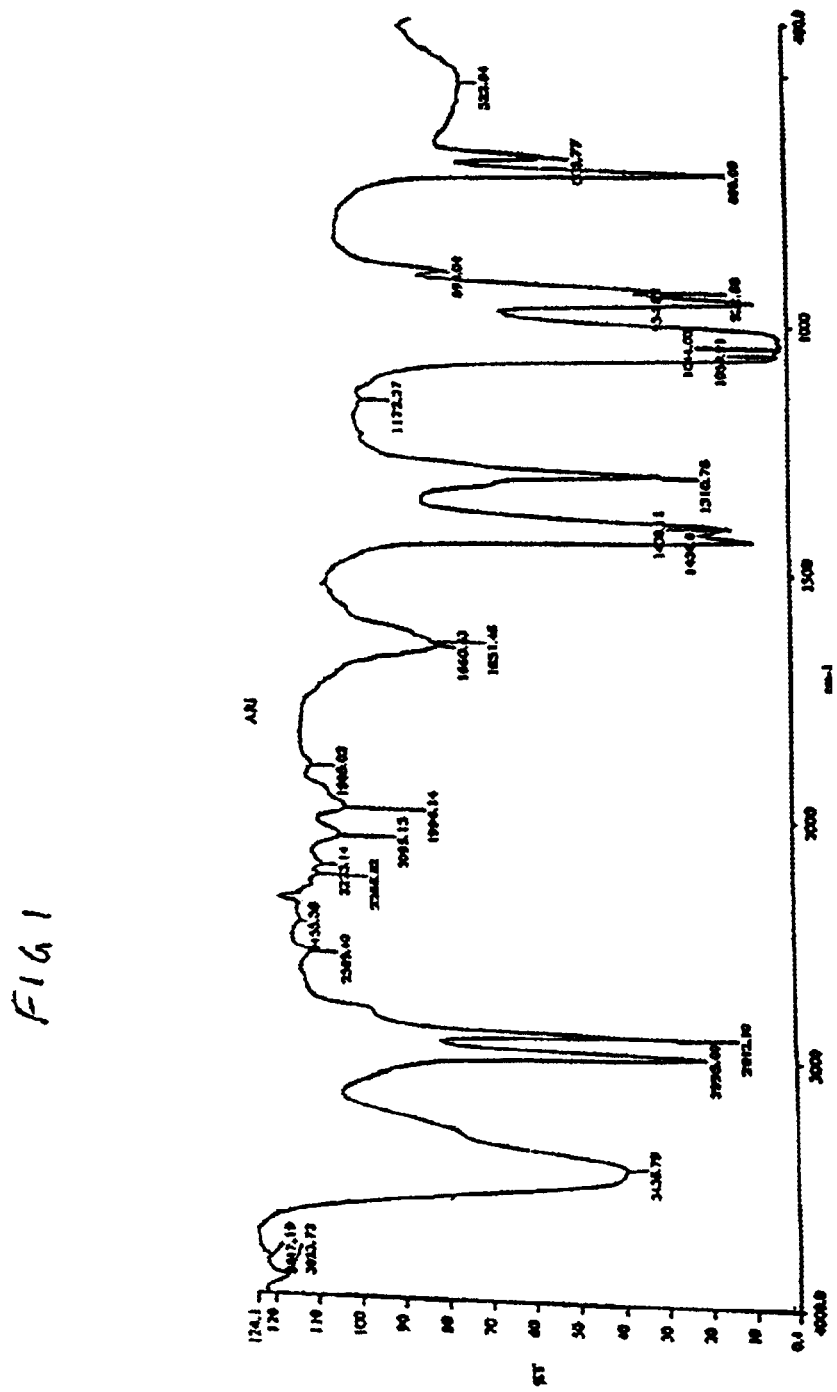
FIG. 1 shows multiple quantum coherence transfer spectra (MQCT) of compound I, 2, 6, dihydroxy, 8, hexoxy, 1, 4, naphthaquinone.

*Aspergillus niger* CFR 1046 isolated from a sample was found to produce new biologically active substance. This substance was extracted from the fermented potato dextrose broth using ethyl acetate followed by column chromatography and crystallization. The purified compound was identified as 2, 6, dihydroxy, 8, hexoxy, 1, 4, naphthaquinone by spectral analysis.

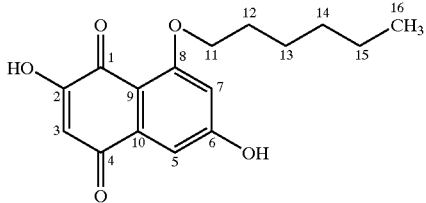

Thus the fermentation of *Aspergillus niger* CFR 1046 or a mutant thereof and suitable isolation techniques may be used to produce the compound of the investigation.

A biologically pure culture of *Aspergillus niger* CFR 1046, from which the compound of investigation was derived, has been deposited with the American Type Culture Collection (ATCC) in Rockville, Md., and has been added to its permanent collection under its accession code ATCC.

A novel substance was isolated from the fermented broth of *Aspergillus niger* species CFR 1046 originally obtained from the CFTRI Culture Collection. The purified compound was found to conform to structure I

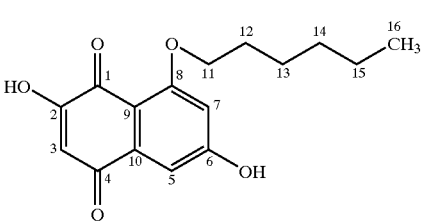

The compound, named by the inventors as SS 140104, is designated as 2, 6, dihydroxy, 8, hexoxy, 1, 4, naphthaquinone. Structure was confirmed by spectral analysis.

Acid or base addition products, e.g., salts, of this compound are also useful. Among the preferred addition products are those containing the ions hydrochloride, hydrobromide, sulfate, sodium, potassium, calcium and the like.

TAXONOMY

Morphology

The fungal mycelium on Czapek's solution agar had abundant erect and crowded conidial structures, which was brownish black in color. Conidial heads were divergent, dense and colonies were wrinkled on the reverse surface. Sclerotia were not observed.

Cultural and Physiological Characteristics

The growth characteristics of CFR 1046 on malt-extract-agar were similar to that of Czapek's solution agar. But the colonies were dark and less dense. The culture grew well at ambient temperature of 26° C., 30° C. Conidial walls were smooth and thick. The length of Conidiophores was 0.67–1.13 mm. Table 1 shows the growth of CFR 1046 in the presence of various carbon and nitrogen sources.

TABLE 1

Growth of CFR 1046 on Czapek's agar in the presence of various carbon and nitrogen sources.

|  | growth | reverse side color Of the plate | spores |
|---|---|---|---|
| C-Source |  |  |  |
| Maltose | very good, | not wrinkled | dark, dense |
| Glucose | good, | not wrinkled | dark, dense |
| Fructose | good | not wrinkled | very dark, very dense |
| Cellobiose | less | not wrinkled | dark, dense |
| Meso-Inositol | good | not wrinkled | dark, less dense |
| Rhamnose | good | not wrinkled | dark, less dense |
| Mannitol | less | not wrinked | dark, less dense |
| Xylose | less | not wrinkled | dark, dense |
| Arabinose | good | not wrinkled | brownish, less dense |
| N-Source (C-Source: Sucrose) |  |  |  |
| Ammonium Sulfate | good, non - sporulating margin | wrinkled | very dark, dense |
| Ammonium Nitrate | good | wrinkled | very dark, dense |
| Ammonium Chloride | good, prominent non sporulating margin | wrinkled | very dark, dense |

Taxonomic Position

The strain of *Aspergillus niger* CFR 1046, isolated locally, was taken from the CFTRI Culture Collection. It was further characterized. The characteristics indicated that the strain belongs to *Aspergillus niger* group. According to the descriptions of Raper and Fennell (Raper K B and Fennell D T (1965) The Genus Aspergillus; The Williams and Wilkins Co, Baltimore, pp 293–310), the strain CFR 1046 is related to *Aspergillus niger* V. Tiegh.

FERMENTATION

Stock Culture and Flask Fermentation

Strain CFR 1406 was propagated on Potato Dextrose Agar (Hi Media Mumbai, India) slant composed of soluble starch 0.4% and glucose 2%. After incubation for 4 days at 30° C., a portion of the mature agar slant was inoculated into 100 ml of Potato Dextrose in a 500 ml Erlenmeyer flask and incubated at 30° C. on a rotary shaker at 250 rpm. The inoculated flasks were incubated for 8 days at 30° C.

Isolation and Purification

Fermented broth (3 L) was treated with ethyl acetate (2 liter) for two hours followed by cheesecloth filtration to remove the biomass and the organic extract was separated from the broth by a separating funnel. This organic extract was dried over anhydrous sodium sulfate and concentrated in vacuo to afford a crude solid (0.42 gm). The residue was re-suspended in chloroform and dry coated on 0.5 gms silica gel. This was loaded on a 5 gm (60–120 mesh) silica gel column (25×1 cm;) packed in hexane. The compound was eluted as a deep yellow band in chloroform:ethylacetate (9:1) fraction. Solvent was evaporated in vacuo to obtain 25 mgs of amorphous red powder, designated as Compound 1.

Physico-chemical Properties

Compound 1, is an amorphous red powder and is soluble in methanol, ethyl acetate, dimethyl sulphoxide, diethyl ether, sodium bicarbonate solution, sodium carbonate solution and sodium hydroxide solution, slightly soluble in chloroform and hexane, but insoluble in water. The physico-chemical properties are given in Table 2. EI-MS spectra of the compound showed the molecular ions at m/z 205. The fragmentation analysis is also given in Table 2.

TABLE 2

Physico-chemical properties of compound 1.

| | |
|---|---|
| Nature: Red amorphous powder. | |
| Melting Point: decomposes at 170–175° C. | |
| $\lambda_{max}$ nm ($\epsilon$) at pH 3.8: | 232 (8,800), |
|  | 265 (12,700), |
|  | 310 (5,900). |
| $\lambda_{max}$ nm ($\epsilon$) at pH 9.0: | 226 (21,600), |
|  | 286 (15,400), |
|  | 355 (5,800). |
| IR: 3437, 2995, 2912 and 1660 cm$^{-1}$. | |
| Molecular formula: $C_{16}H_{18}O_5$ | |
| EI-MS m/z: | 290 − 85 = 205$^{M+1}$ |
|  | 206 − 28 = 178 |
|  | M$^+$—CO |
|  | 178 − 28 = 150 |
|  | —Co |
|  | 150 − 42 = 108 |
|  | 108 − 27 = 81 |
| HPLC (Rt): 4.5 min (column: RP-C18, 25 × 4.6 mm, | |
| Mobile phase: methanol, 0.5 ml/min, 265 nm) | |
| GC (Rt): 21.4 min (column: HP-5, Conditions: 50° C., | |
| 2 min, 10° C./min; 220° C., 2 min, 15° C./min; 270° C., 20 min.) | |

The molecular formula of compound was established as $C_{16}H_{18}O_5$, based on the mass spectra and $^1H$ and $^{13}C$-NMR spectra (Table 3).

TABLE 3

$^1H$ NMR spectra (500 MHz in DMSO-d$_6$) and $^{13}C$ NMR spectra (500 MHz in DMSO-d$_6$) of compound 1

|  | $^1H$ ($\delta$, ppm) | $^{13}C$ ($\delta$, ppm) |
|---|---|---|
| 16 CH$_3$ | 0.8 | 29.9$^a$ |
| 11 CH$_2$ | 1.0 | 31.5 |
| 12, 13, 14 CH$_2$ | 1.2 |  |
| 15 CH$_2$ | 1.5 | 39.9–40.9 |
| H-7 | 6.0 | 111.1 |
| H-3 | 6.5 | 108.9 |
| H-5 | 6.95 | 108.2 |
| 4-CO | — | 190.83$^a$ |
| 1-CO | — | 181.7$^a$ |
| 6-OH | — | 164.4$^a$ |
| 2-OH | — | 163.6$^a$ |
| 8-O | — | 160.9$^a$ |

$^a$Carbon-13 assignments are interchangeable.

Figure 2:
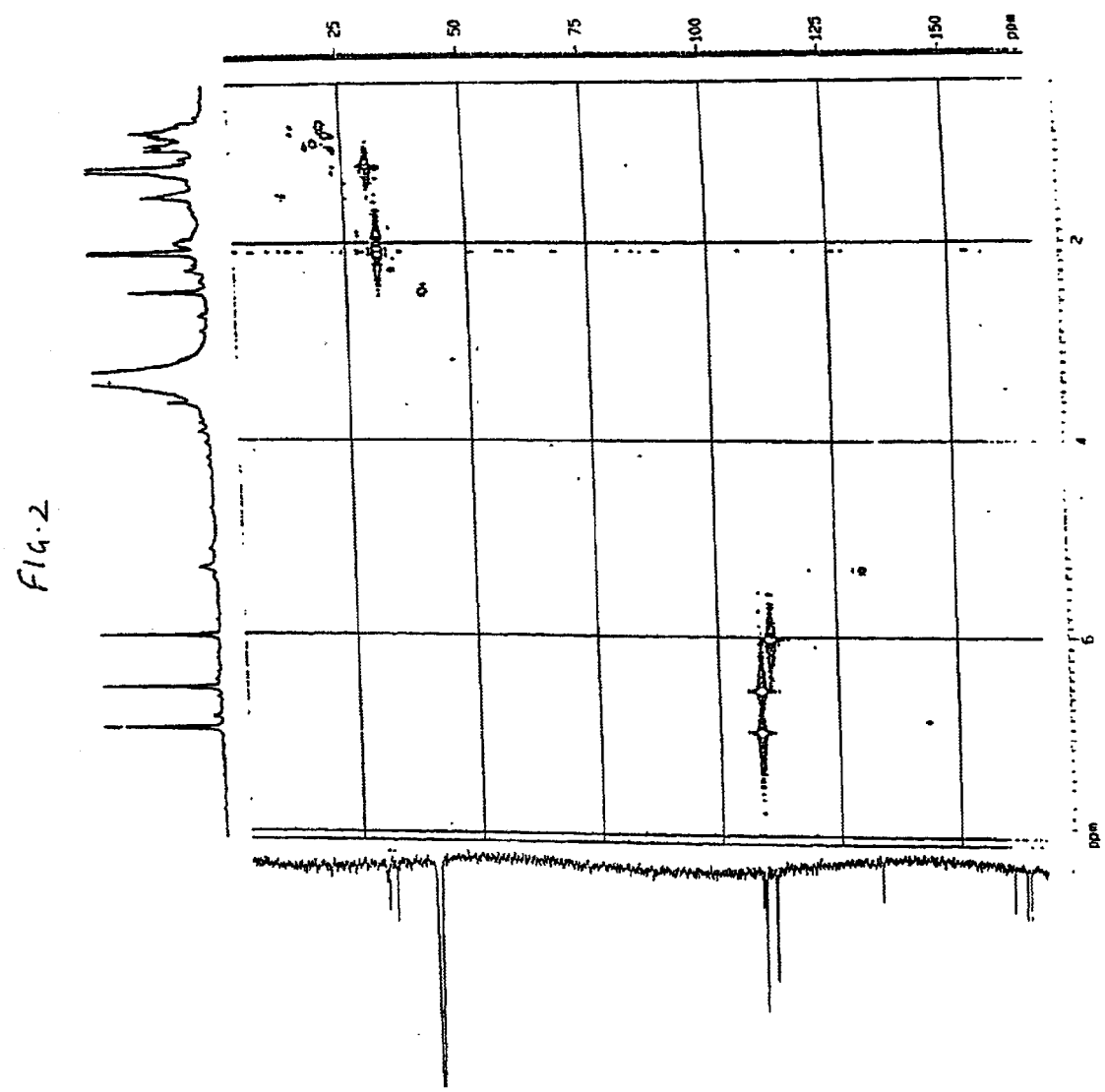
FIG. 2 shows the mass spectrum of compound I, 2, 6, dihydroxy, 8, hexoxy, 1, 4, naphthaquinone.
Figure 3:
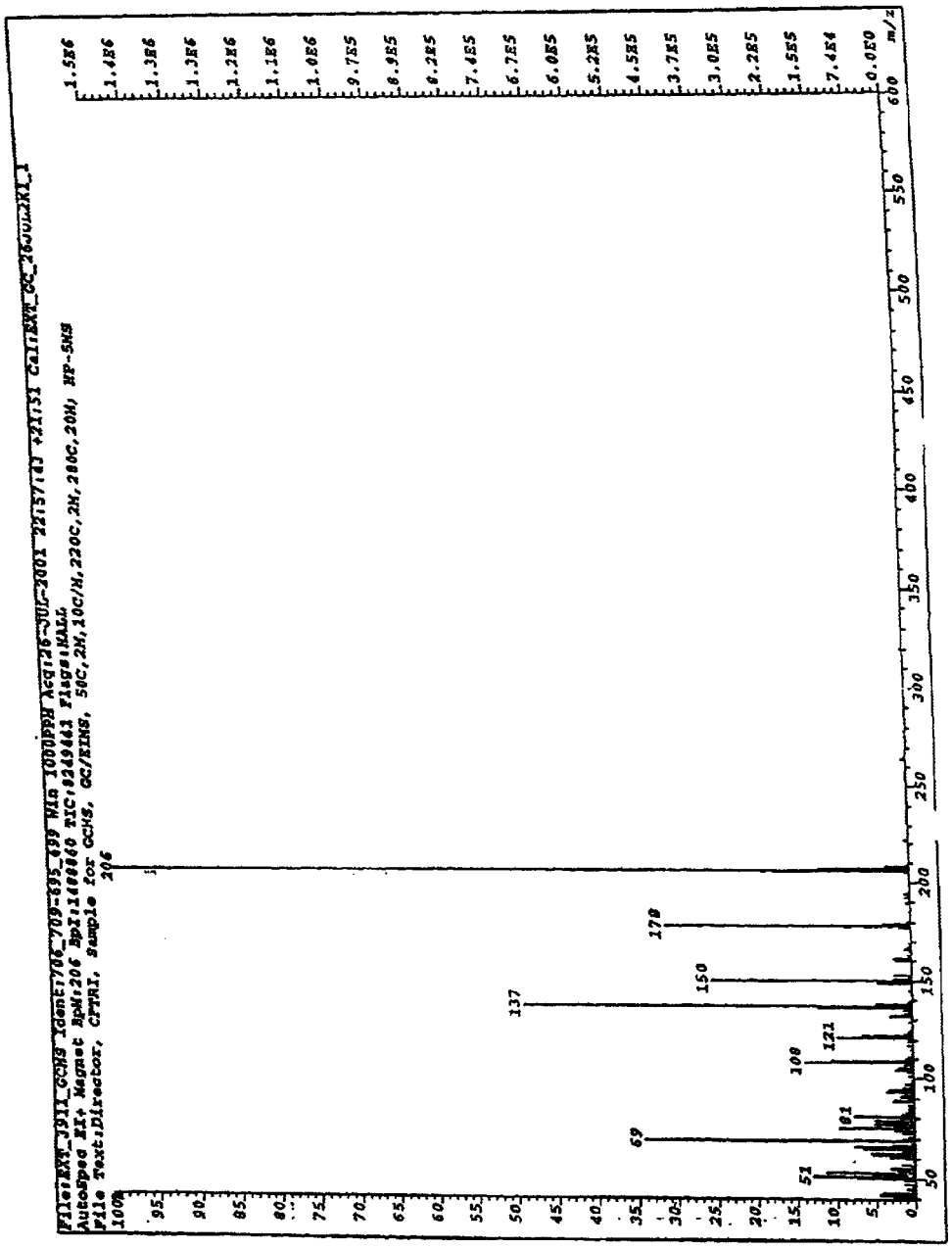
FIG. 3 shows the Mass fragmentation Spectra of Compound I.

The physico-chemical data are summarized in Table 2. The UV spectra of this substance had an absorption maxima at pH 3.8 are 232, 265, 310 and at pH 9.0 are 226, 286, 355. The IR spectrum (FIG. 1) of compound 1 shows typical absorption bands at 3437, 2995, 2912 and 1660 cm$^{-1}$. The $^1H$-NMR spectral data (FIG. 2) of this compound and the $^{13}C$-NMR spectral data (Table 3 and FIG. 2) and the Mass fragmentation Spectra (FIG. 3) of the compound are given Structure Determination The spectral characteristics and other properties of the compound isolated are shown in Table 2 and Table 3 above. The compound exhibits UV absorption at 232 nm, 265 nm and 310 nm at pH 3.8. However at pH 9.0, while the $\lambda_{max}$ at 232 nm showed a hypochromic shift to 226 nm both the 265 nm peak and 310 nm peak showed a bathochromic shift to 286 nm and 355 nm respectively. This indicates that there are ionizable phenolic groups on aromatic rings. The broad IR absorption at 3437 $Cm^{-1}$ indicates —OH stretching frequencies. The peak at 2995 $Cm^{-1}$, 2912 $Cm^{-1}$ indicate aromatic C—H stretching. A broad ketonic absorption bond in IR spectrum at 1660 $Cm^{-1}$ indicating probably hydrogen bonded keto group. Another conformation of stretching was obtained from two dimensional heteronuclear multiple quantum coherence transfer spectra (2DHMQCT). An aliphatic group corresponding to six carbons were observed at 0.8 ($CH_3$) and 0.8, 1.0, 1.2 and 1.5 (5-$CH_2$) ppm. The —$CH_2$ at 1.0 ppm might have come from —$CH_2$ group of hexyl moiety being subjected to ring current effect of the aromatic group present. Three separate single signals were seen at 6.0, 6.5 and 6.95 ppm, indicating aromatic protons. The corresponding $^{13}C$ signals are as follows;

29.9 (—$CH_3$), 31.5 (—$CH_2$), 39.9 to 40.9 (—$CH_2$), 111.1 (Ar—H), 108.9 (Ar—H), 108.2 (Ar—H), 190.8 (CO), 181.7 (CO), 164.4 ($C_{Ar}$—OH), 163.6 ($C_{Ar}$—OH), 160.9 ($C_{Ar}$—O) EIMS analysis showed a parent peak at 205 ($M^+$) other fragment peaks like 178 ($M^+$—CO), 150 (—CO), 108 and 81 clearly indicating aromatic group of the molecule. However, parent ion peak was distinctly missing. Based on EIMS and 2DHMQCT analysis the proposed structure is given below:

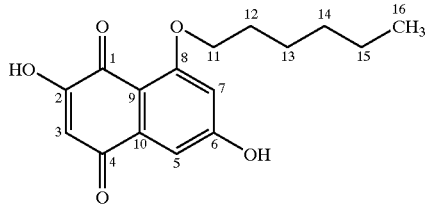

Compositions and Methods

In this description of the invention, references to the compound of formula I is intended to include all pharmaceutically acceptable derivatives of the same.

The novel compounds of the invention can be used in a variety of pharmaceutical dosage forms. Thus, oral, parental, nasal, topical, buccal, ocular and other forms can be used. When such forms are formulated they will include pharmaceutically acceptable excipients such as colorants, carriers, perflumes, stabilizers, flow modifiers and the like in suitable amounts (i.e., from 0.001 to 0.99 wt %).

The compound of the invention is useful in methods of inhibiting the effects of rat lens aldose reductase The compound of formula I may also be used to treat a host, preferable a mammal, which is suffering from a disorder associated with a metabolism of Aldose reductase, such as those arising from diabetes related complication such as neuropathy, nephropathy and cataract.

Acid or base addition products, e.g., salts, of this compound are also useful. Among the preferred addition products are those containing the ions hydrochloride, hydrobromide, sulfate, sodium, potassium, calcium and the like.

The following example illustrates the Aldose reductase inhibitor effects of the novel compound.

Experimental

Lens were collected from rat eyes and homogenized with sodium, potassium phosphate buffer (0.135 M, pH 7.0) containing 0.5 mM of phenyl methyl sulphonyl fluoride and 10 mM of β-mercaptoethanol. The homogenate was centrifuged at 10,000 r.p.m for 30 minutes at 4° C. The supernatant was taken as enzyme source. Enzyme reaction was carried out at 25° C. in a quartz cuvette with a 1 cm light path. The assay mixture contained 100 μL of nicotinamide adenine dinucleotide phosphate tetra sodium salt (from a stock solution of 9.6 mM), 100 μL of DL-glyceraldehyde (from a stock solution of 250 mM), 10 μL of inhibitor dissolved in dimethyl sulphoxide, sodium-potassium-phosphate buffer (0.135 M, pH 7.0) to make up the total volume to 3 mL and the reaction was initiated by the addition of 200 μL of enzyme solution. The enzyme reaction was monitored by the decrease in absorbence at 340 nm and compared with enzyme reaction without inhibitor.

Results

The compound (I) was discovered in the fermented bran of a species of *Aspergillus niger* CFR 1046. The compound was successfully purified to homogeneity. The $IC_{50}$ value of the compound against rat lens aldose reductase inhibitory activity was determined to be 26.2 μM.

Reasonable variations, such as those that would occur to a skilled artisan, can be made herein without departing from the scope of the invention.

We claim:

1. An aldose reductase inhibitor of the formula I or a pharmaceutically acceptable derivative thereof.

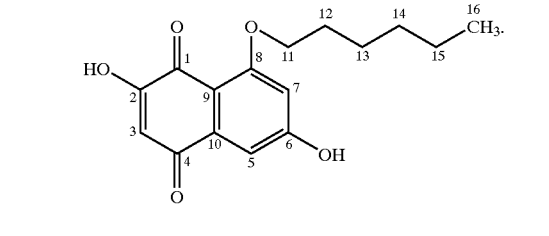

2. An aldose reductase inhibitor of claim 1, wherein the derivative is an acid or base addition product.

3. A pharmaceutical preparation containing the compound of claim 1, and one or more pharmaceutically acceptable excipients.

4. An aldose reductase inhibitor of claim 1, wherein said inhibitor is a rat lens aldose reductase inhibitor.

5. An aldose reductase inhibitor of claim 1, wherein the aldose reductase inhibitor of formula I is 2,6-dihydroxy-8-hexyloxy-1,4-naphthaquinone.

6. A process for the isolation of an aldose reductase inhibitor of the formula I

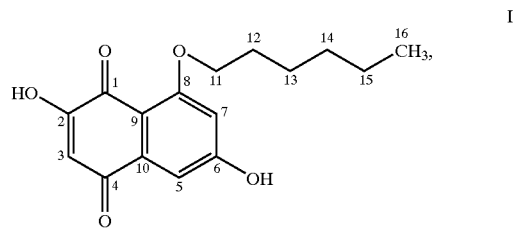

comprising culturing *Aspergillus niger* CFR 1046 and isolating said aldose reductase inhibitor from the resulting fermentate.

7. A process as claimed in claim 6, wherein the aldose redudase inhibitor isolated from *Aspergillus niger* CFR 1046 is 2,6-dihydroxy-8-hexyloxy-1,4-naphthaquinone.

8. A process as claimed in claim, 6, wherein the compound of formula I is isolated from fermentates of *Aspergillus niger* CFR 1046 by solvent extraction.

9. A process as chimed in claim 6, wherein the compound of formula I is isolated from fermentates of *Aspergillus niger* CFR 1046 by column chromatography.

10. A process as chimed in claim 6, wherein the compound of formula I is isolated from fermentates of *Aspergillus niger* CFR 1046 by crystallization.

11. A process as chimed in claim 6, wherein the compound of formula I is isolated from fermentates of *Aspergillus niger* CFR 1046 from fermented potato dextrose broth using ethyl acetate solvent followed by column chromatography and crystallization.

12. A process, wherein the compound of formula I according to claim 1, isolated from fermentates of *Aspergillus niger* CFR 1046, is converted into a pharmaceutically acceptable derivative.

13. A process as claimed in claim 12, wherein the pharmaceutically acceptable derivative comprises acid or base addition products of said compound.

14. A process as claimed in claim 13, wherein the addition products contain hydrochloride, hydrobromide, sulfate, sodium, potassium, calcium and the like ions.

* * * * *